United States Patent
Avni et al.

(10) Patent No.: US 6,273,863 B1
(45) Date of Patent: Aug. 14, 2001

(54) ADAPTIVE WEIGHT BEARING MONITORING SYSTEM FOR REHABILITATION OF INJURIES TO THE LOWER EXTREMITIES

(75) Inventors: Arik Avni, Bat-Yam; Inna Sosman, Arad, both of (IL)

(73) Assignee: Andante Medical Devices, Ltd., Beer Sheva (IL)

(*) Notice: Subject to any disclaimer, the term of this patent is extended or adjusted under 35 U.S.C. 154(b) by 0 days.

(21) Appl. No.: 09/439,007

(22) Filed: Nov. 12, 1999

Related U.S. Application Data

(60) Provisional application No. 60/161,433, filed on Oct. 26, 1999.

(51) Int. Cl.⁷ .............................. A61B 5/103; A61B 5/117
(52) U.S. Cl. .............................................................. 600/587
(58) Field of Search .................................... 600/587, 592, 600/595; 361/291; 340/573.1, 272, 323, 573; 73/172; 128/782; 272/97; 601/105; 602/19

(56) References Cited

U.S. PATENT DOCUMENTS

| | | | |
|---|---|---|---|
| 3,974,491 | 8/1976 | Sipe | 340/272 |
| 4,267,728 | 5/1981 | Manley et al. | 73/172 |
| 4,416,293 | 11/1983 | Anderson et al. | 128/782 |
| 4,426,884 | 1/1984 | Polchaninoff | 73/172 |
| 4,503,705 | 3/1985 | Polchaninoff | 73/172 |
| 4,510,704 | 4/1985 | Johnson | 36/136 |
| 4,516,110 | 5/1985 | Overmyer | 340/323 |
| 4,629,181 | 12/1986 | Krive | 272/97 |
| 4,647,918 | 3/1987 | Goforth | 340/573 |
| 4,703,445 | 10/1987 | Dassler | 364/561 |
| 4,745,930 | 5/1988 | Confer | 128/779 |
| 4,813,436 * | 3/1989 | Au | 600/592 |
| 4,814,661 | 3/1989 | Ratzlaff et al. | 310/328 |
| 4,824,107 | 4/1989 | French | 273/1 GC |
| 4,858,599 | 8/1989 | Halpern | 601/105 |
| 4,884,223 | 11/1989 | Ingle et al. | 364/550 |
| 4,906,192 | 3/1990 | Smithard et al. | 434/253 |
| 4,919,418 | 4/1990 | Miller | 272/129 |
| 4,928,959 | 5/1990 | Bassett et al. | 272/96 |
| 5,042,504 | 8/1991 | Huberti | 128/779 |
| 5,107,854 | 4/1992 | Knotts et al. | 128/779 |
| 5,209,240 | 5/1993 | Jain et al. | 128/779 |
| 5,230,249 | 7/1993 | Sasaki et al. | 73/714 |
| 5,269,081 | 12/1993 | Gray | 36/136 |
| 5,285,022 | 2/1994 | Antone | 177/253 |

(List continued on next page.)

Primary Examiner—John P. Lacyk
Assistant Examiner—Brian Szmal
(74) Attorney, Agent, or Firm—Woodcock Washburn Kurtz Mackiewicz & Norris LLP

(57) ABSTRACT

A portable, self-learning adaptive weight bearing monitoring system for personal use during rehabilitation of orthopedic patients with fractures of the lower extremities. The system includes a flexible insole which is worn inside the shoe. The insole includes pressure and/or force sensor that measure the GRF force applied at key bearing points under the foot or other portions of the patient's lower extremity. The sensors are, in turn, connected through an A/D converter to a CPU that is connected so as to drive a stimulator that delivers closed-loop sensory stimulation (electrical, mechanical, and/or audio) as feedback to encourage the patient to load the optimal target weight for the limb for which the weight bearing force is being measured. Accurate real-time monitoring of the weight bearing during physical rehabilitation is also provided, and, through the use of closed-loop sensory stimulation, the patient is given continuous feedback for improving rehabilitation.

15 Claims, 6 Drawing Sheets

U.S. PATENT DOCUMENTS

| | | | |
|---|---|---|---|
| 5,323,650 | 6/1994 | Fullen et al. | 73/172 |
| 5,325,869 * | 7/1994 | Stokes | 600/592 |
| 5,357,696 | 10/1994 | Gray et al. | 36/136 |
| 5,408,873 | 4/1995 | Schmidt et al. | 73/862.625 |
| 5,619,186 | 4/1997 | Schmidt et al. | 340/573 |
| 5,655,316 | 8/1997 | Huang et al. | 36/132 |
| 5,659,395 | 8/1997 | Brown et al. | 356/376 |
| 5,790,256 | 8/1998 | Brown et al. | 356/376 |
| 5,813,142 | 9/1998 | Demon | 36/29 |
| 5,827,209 | 10/1998 | Gross | 602/19 |
| 5,840,047 | 11/1998 | Stedham | 600/587 |
| 5,877,687 | 3/1999 | Bernard et al. | 340/573 |
| 6,033,370 * | 3/2000 | Reinbold et al. | 600/595 |
| 6,087,926 * | 7/2000 | Hajianpour | 340/573.1 |

* cited by examiner

Diagram of control

ADAPTIVE WEIGHT BEARING MONITORING SYSTEM FOR REHABILITATION OF INJURIES TO THE LOWER EXTREMITIES

CROSS-REFERENCE TO RELATED APPLICATIONS

The present application claims priority from U.S. Provisional Application No. 60/161,433 filed Oct. 26, 1999, the contents of which are incorporated herein by reference.

BACKGROUND OF THE INVENTION

1. Field of the Invention

The present invention relates to a rehabilitation system for use by orthopedic patients after fracture injury or joint replacement, by patients inflicted by neurological conditions such as cerebral vascular accident (CVA) and cerebral palsy (CP), by patients subsequent to lower limb amputation, and by patients rehabilitating from sports injuries such as meniscial, ACL or achilles tendon tears and, more particularly, to a portable, self-learning adaptive weight bearing monitoring system for rehabilitative use by such patients.

2. Description of the Prior Art

In the United States alone, millions of people each year suffer from serious leg injuries that require prolonged physical therapy. More than 500,000 hip and knee replacements are performed every year. Also, over 250,000 hip fractures, most of them requiring open reduction and internal fixations, are noted yearly in the United States. In addition, the number of multiple trauma victims with lower extremity fractures that require rehabilitation is also substantial. Many individuals who have suffered a stroke also may be required to relearn the ability to control their body in a three-legged stance. Indeed, there are estimated to be almost 9,000 rehabilitation and physical therapy units in the United States that address such injuries and more than twice that number worldwide.

During the rehabilitation of a simple fracture, the conventional medical approach has been a partial weight bearing (PWB) approach. The PWB approach is recommended when a soft callus is evident on an x-ray typically taken 2 to 6 weeks after the injury. However, in the case of a complicated fracture, such as an intra-articular injury, the weight bearing is typically completely prohibited until 3 months post-injury, and only then is the PWB approach prescribed. While weight bearing is essential for the bone building process, an overload can damage the bone fixation and the healing process. Hence, PWB as a prescription is problematic because it is subjective and the patient must decide by himself/herself how much to load the injured limb.

However, several devices are known in the prior art that assist the therapist and patient in determining how much weight is being applied to a patient's lower extremity and include external limb overload warning devices that warn the patient of an overload or an underload in the amount of pressure placed on the leg. For example, Schmidt et al. describe in U.S. Pat. No. 5,619,186 a foot weight alarm device including a foot-shaped insole device including resistive force sensors that fits inside the patient's shoe to warn the patient when the patient is putting too little or too much weight on a limited weight bearing foot. The foot weight alarm device also includes a shoe pouch which laces in the shoe, a foot weight alarm unit which fits in the shoe pouch and contains electronics that connects to the insole device, a data cable that is used by a health care professional to program the foot weight alarm unit, and a foot weight alarm calibration system used by the health care professional to program the foot weight alarm unit. The foot weight alarm unit measures the forces on each insole's sensors to compute the total force, and when the total force is below the target value, a low tone is produced by the foot weight alarm unit, while in the target zone a high tone is produced and above the target zone a two-tone warble is produced to inform the patient to take weight off the limb. Other features of the Schmidt et al. foot weight alarm device include an optimal data-logging feature that logs the time and maximum weight of each step for up to 16,000 steps. This feature provides the physician with the ability to review the patient's progress while at, and after leaving, the rehabilitation facility. In addition, a motion detector turns on the foot weight alarm device when the first step is taken by the patient, and power saving electronic circuitry turns the device off when there is no weight on the foot, thereby saving energy.

Unfortunately, the foot weight alarm disclosed in the afore-mentioned Schmidt et al. patent is limited in that it is passive and provides limited information to the patient and the physician. In particular, while the foot weight alarm device provides biofeedback data relating to the weight force applied to the foot, it does not provide electrical stimulation to adjust the patient's gait. Rather, only a passive alarm is provided. In addition, the rehabilitation program using the foot weight alarm device is, by necessity, based on a subjective estimation of the maximal weight bearing the foot may accept, as opposed to objective parameters that are personalized to the patient. Moreover, the foot weight alarm device requires continuous professional supervision. A sensor device is desired that allows the patient to continue his or her rehabilitation program at home without the need for such continuous professional supervision.

Other weight sensor devices are also known which allow the physician to monitor the force applied to a lower extremity by a patient. For example, the so-called "ForceGuard" described in U.S. Pat. No. 5,107,854 has been used in the prior art to sense the amount of weight applied to the plantar surface of the foot. This device alerts the wearer and/or therapist with a repeating tone when the weight exceeds the pre-elected value. Typically, the ForceGuard device is used to train patients in limited weight-bearing accurately and consistently to the physicians' order, to report the results of training, and to provide data for consideration by monitoring physicians. In use, the physician's orders may be pound limits, percentages of body weight, or other phrases. Typically, the pound limits are rounded to the next lower setting on the ForceGuard weight-bearing monitor, where a typical setting is 20, 30, 50, 70, or 90 pounds. When the percentage of body weight limit is set, the setting is calculated by multiplying the total body weight by the percent ordered. As before, the percentage limit is typically rounded to the next lower setting on the ForceGuard weight-bearing monitor. In the ForceGuard device, toe touch weight bearing is interpreted as 20 pounds, unless the physician states otherwise. A toe touch pattern is accomplished with normal gait and stance, but less than 20 pounds force through the lower extremity. On the other hand, partial weight bearing is interpreted as 30 percent of patient body weight unless the physician specifies a different limit.

By way of example, ForceGuard Model 2090 consists of 3 components including an electronic module, a foot pad, and a leg band. The leg band is worn around the patient's ankle, and the electronics module is attached to the leg band. The foot pad, a flexible, fluid filled chamber, plugs into the electronics module and is worn under the plantar surface of the patient's foot inside suitable footwear. The foot pad senses the weight being placed through the patient's lower extremity. The electronics module functions as the user interface that processes information from the foot pad and produces an alarm when the weight on the foot pad exceeds the selected weight.

While the ForceGuard device and other weight monitoring devices are known in the art that measure, in one fashion or another, the forces that are applied to a patient's foot, no devices known to applicant provide sensory stimulation, such as electrical or mechanical vibration, that affects the patient's gait or provide a personalized rehabilitation program whereby objective parameters may be used to personalize the rehabilitation to the patient without the requirement of continuous professional supervision. A device with these and other improved characteristics is desired.

SUMMARY OF THE INVENTION

The present invention is a portable rehabilitation system that includes a flexible insole which is worn inside the shoe. The insole includes at least one pressure and/or force sensor that measures the force applied under the foot. The sensor is, in turn, connected through an Analog-to-Digital (A/D) converter to a Central Processing Unit (CPU) that is connected so as to drive an electrical and/or mechanical stimulator that delivers closed-loop electrical or mechanical stimulation as feedback to encourage the patient to load the optimal target weight for the limb for which the weight bearing force is being measured. The present invention thus provides accurate real-time monitoring of the weight bearing during physical rehabilitation and, through the use of closed-loop sensory stimulation, gives the patient continuous feedback and feedforward data for improving rehabilitation.

In a preferred embodiment, the CPU implements an algorithm that provides feedback based on the forces acting on the lower limb during a stance and also provides feedforward of the information logged. By analyzing the weight placed during past strides, for example, the present invention may predict the optimal weight load of the next stride, act to correct improper weight placement, and teach the patient to load the optimal weight during the rehabilitation period. The present invention thus provides a feedback weight-bearing monitoring system which improves upon prior art devices that are based on subjective estimation of maximal weight bearing and that provide only a simplistic warning tone when thresholds are exceeded. Also, the preferred embodiment of the present invention further measures short term and long term changes in dynamic weight bearing and records these changes. Correcting feedforward stimulation tells the patient to increase or decrease the load, and to load around an optimal target.

The present invention also allows for the prescription of a personal rehabilitation program for individual patients that is based on biomechanical bone characteristics and bone fixation properties of the injured person (module elastic, bone density, etc.) as well as on objective characteristics of the patients (age, gender, weight, fracture type, etc.). These and other characteristics of the invention will be described in more detail below.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENTS

Figure 1:
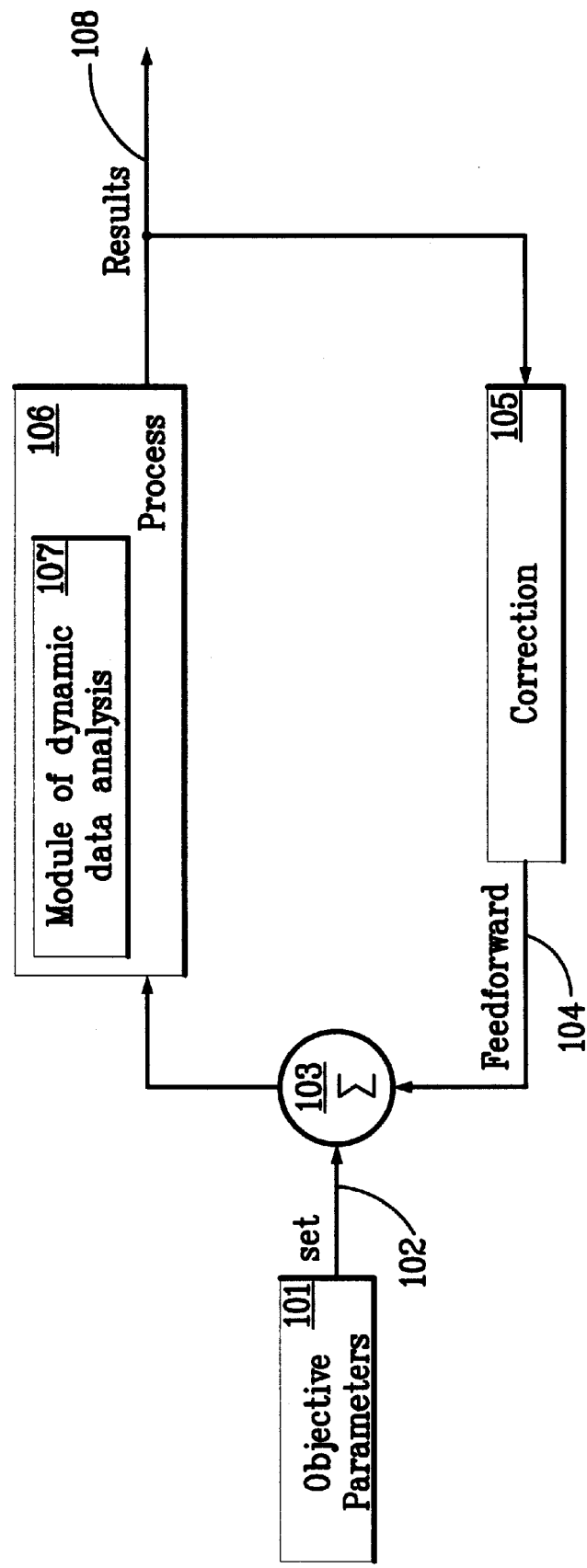
FIG. 1 illustrates the feedforward design of a preferred embodiment of the invention.

A system which meets the above-mentioned objects and provides other beneficial features in accordance with the presently preferred exemplary embodiment of the invention will be described below with reference to FIGS. 1–4. Those skilled in the art will readily appreciate that the description given herein with respect to those figures is for explanatory purposes only and is not intended in any way to limit the scope of the invention. Throughout the description, like reference numerals will refer to like elements in the respective figures.

Definitions

For a better understanding of the invention, the following definitions of the key terms used herein will be used throughout the specification.

Biofeedback is a training technique for improving patient's performance, using an external feedback, which creates an unconscious physiological reaction.

Feedforward is a generalization of biofeedback. Feedforward is a training technique for improving patient's performance that provides feedback prior to the predicted physiological reaction. As part of general reaction, feedforward includes biofeedback.

Dynamic input signals $f_{ij}$ are control parameters of the weight bearing process monitored using the sensors of the invention.

Static inputs are the patient's individual objective parameters such as age, gender, type of fracture, biomechanical properties of fixation, and the like. In the time frame of the rehabilitation period, these parameters are constant.

Quasi-constant parameters such as time post injury, weight, etc. change during the whole rehabilitation period, but are constant during one gait cycle.

Target value of the weight bearing process $f_{to}$ is the weight bearing (WB) amount prescribed by the physician or calculated using historical weight bearing data.

Upper limit of the weight bearing process $f''_{th}$ is the maximum allowed value of the control parameters.

Lower limit of the weight bearing process $f'_{th}$ is the minimum allowed value of the control parameters.

Output signals $Y_i$ are electrical and/or mechanical stimulating signals and/or audio-visual signals.

Electrical stimulation is the process of applying square shaped symmetrical, biphasic, low frequency (up to 20 Hz) electrical pulses to the patient's body.

Mechanical vibration is the process of applying mechanical tactile stimulus to the patient's body.

System Description

FIG. 1 generally illustrates the feedforward design of a preferred embodiment of the present invention. As noted above, objective parameters 101 are provided which may include static inputs such as age, gender, type of fracture, fracture geometry, biomechanical properties of fixation, and the like, and quasi-static inputs such as time post-injury, weight, and the like. The objective parameters 101 are fed into the system to form a set 102 which is unique for the current patient. The set 102 is input into a summer 103 for modification by the feedforward values 104 from correction circuit 105. As will be explained in more detail below, with the beginning of operation, dynamic inputs, such as the sensor inputs, are also collected and undergo calculations in processing system 106, typically in a dynamic data analysis module 107. As result of the analysis in dynamic data analysis module 107, stimulation signals are outputted as results 108. Since the system is a closed-loop system, the quasi-constant parameters are recalculated according to the dynamic inputs and decision rules. The correction circuit 105 generates the feedforward values 104 from results 108 in a manner to be described in more detail below.

Dynamic Data Analysis

Figure 2:
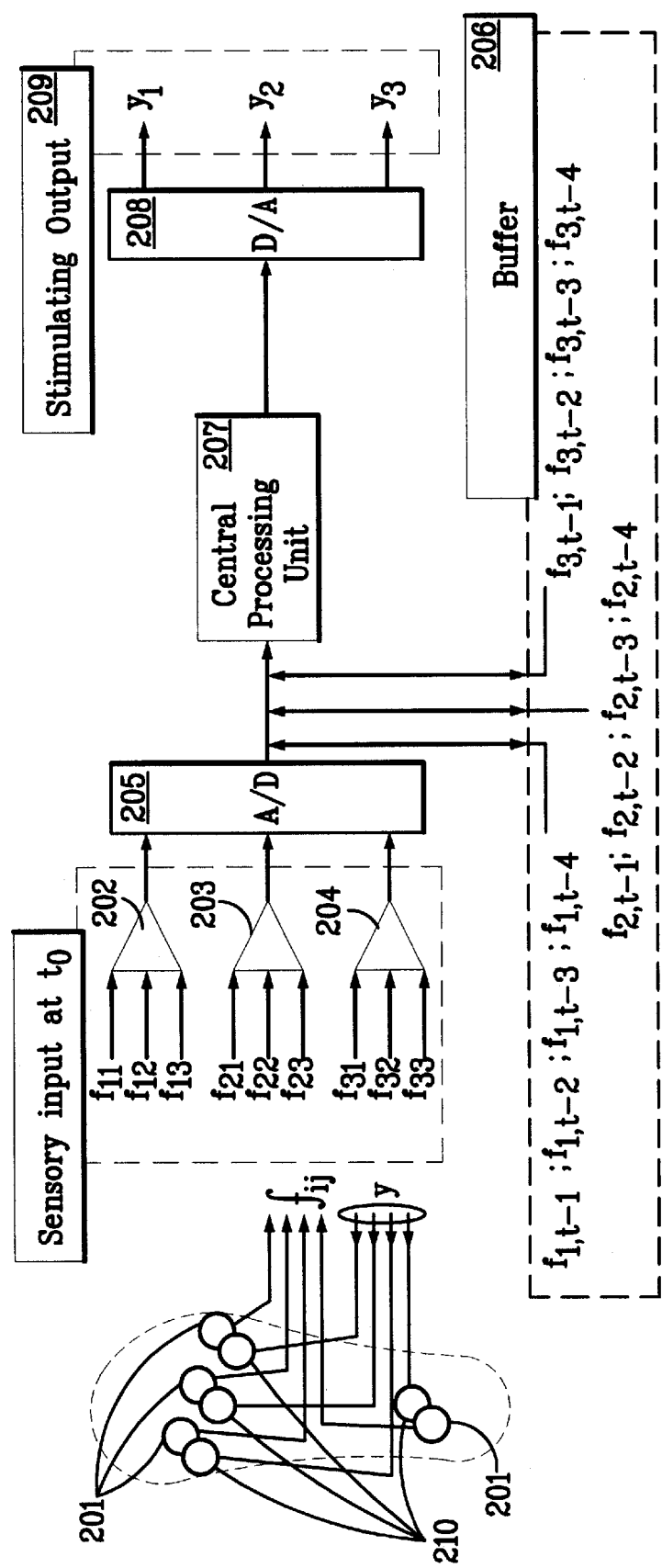
FIG. 2 illustrates the operation of the dynamic data analysis block of FIG. 1 in more detail.

FIG. 2 illustrates the operation of dynamic data analysis block 107 in more detail. As shown, one or more sensory electrodes (sensors) 201 is embedded into the insole (force sensor) or outside the insole (pressure sensor). In a preferred embodiment, the sensory electrode 201 is a pressure sensor, force sensor or other suitable electrode that measures the vertical Ground Reaction Force ("GRF") during the stance phases under one or more key foot locations such as the heel, the $1^{st}$ metatarsal head, the $5^{th}$ metatarsal head, and the hallux. The outputs of sensory electrode 201 are amplified by an amplifier 202, which may be, e.g., a differential amplifier. The sensory electrode 201 provides sensory information $f_{ij}$ on the GRF at a specific time frame $t_0$. These amplified analog signals are then converted into digital signals by A/D converter 203. Upon conversion, these signals are stored in memory buffer 204, which is preferably a First-In-First-Out (FIFO) queue.

Previously converted analog signals from former time frames $t_{-1}$, $t_{-2}$, $t_{-3}$, etc. from memory buffer 204 and the current digital force information from the sensory electrode 201 (actually, the sensory input at time $t_o$) are fed to the CPU 205, which performs necessary calculations of the type described below. As a result of these calculations, according to the 'decision rules' described below, an output signal 206 is provided by CPU 205 to digital-to-analog converter 207. Digital output from CPU 205 undergoes conversion to analog in D/A converter 207 to provide stimulation outputs 208 that are applied to the patient's skin via stimulation electrodes 209. Of course, sensory electrodes 201 and stimulation electrodes 209 may be combined into common transducers, as desired.

Figure 3:
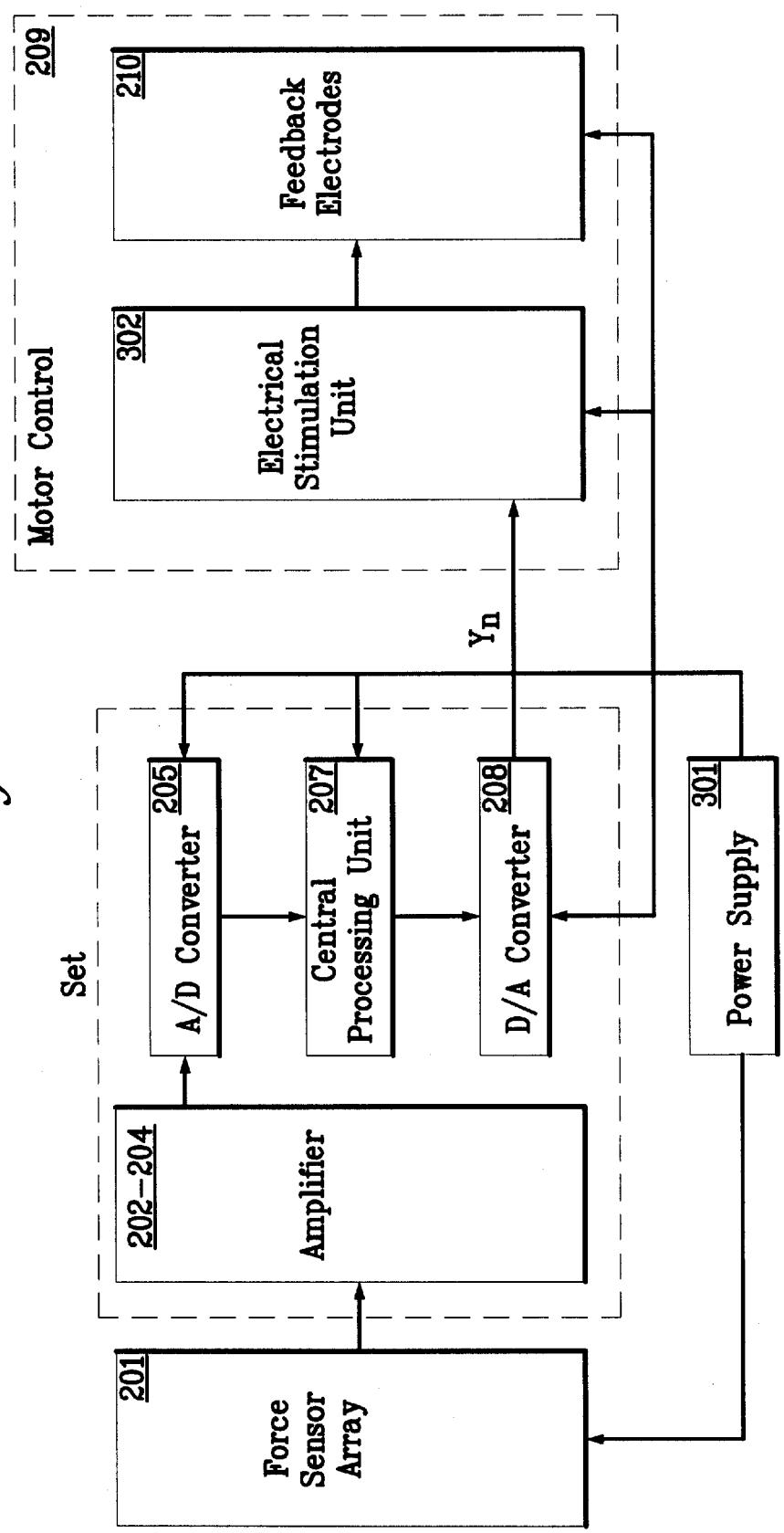
FIG. 3 illustrates the hardware of the system of FIG. 2 with the addition of the power supply and sensory stimulation unit.

The system of FIG. 2 is thus based upon the following components: a power supply (not shown), A/D converter 203, D/A converter 207, sensory electrodes 201, stimulating electrodes 209, amplifier 202, and CPU 205. As illustrated in FIG. 3, the system of the invention is operated by a low-voltage electricity source, such as a direct current power source (battery) or accumulator 301. As known by those skilled in the art, the power supply 301 must comply with FDA and CE requirements for medical equipment. Preferably, the power supply 301 provides regulated voltage to the pressure or force sensors 201, to the CPU 205, to the A/D converter 203, to the D/A converter 207, to the electrical and/or mechanical stimulation unit 302, and to the sensory feedback electrodes 209. Preferably, the sensory electrodes 201 are embedded in a patient' insole at least at three different locations according to the critical points of weight bearing. Sensory electrodes 201 are connected to the power supply 301 and via amplifier 202 to A/D converter 203 for conversion of the analog force sensor output to digital form.

CPU 205 is preferably a single microprocessor that performs any necessary calculations (data processing) and controls sensory stimulation in response to the processed output by way of electrical and/or mechanical stimulation signals and audio-visual signals. The output of CPU 205 is provided to D/A converter 207 for conversion to analog format and transfer to the electrical and/or mechanical stimulation unit 302 for the creation of stimulation signal y. The stimulation signals y are then applied to feedback electrodes 209 or any loudspeakers for generation of an alarm, as appropriate. As shown in FIG. 3, mechanical/electrical stimulation unit 302 and feedback electrodes 209 may together constitute a motor control circuit 303 for the patient's limb.

Software

The processing software implemented in CPU 205 will now be described with respect to the flow charts of FIG. 4(A) through FIG. 4(C). As illustrated, processing begins at step 400 (FIG. 4(A)), and initialization and calibration functions are performed at step 402. In particular, subjective parameters such as age (A), gender (G), type of fracture ($F^T$), date of injury ($F^A$), and patient's weight (W) are input at step 402A, while objective parameters such as initial target value of weight bearing ($f^o_t$) and a kernel for feedforward calculations (M) are fed into system at step 402B. Those skilled in the art will appreciate that age is a significant subjective parameter since the strength of bone decreases somewhat with increasing age and since there is a reduction in Modulus of Elasticity as well as in bone density and blood circulation with increasing age. In addition, there is a sub-periosteal formation and endosteal resorption with increasing age. Gender is also significant since the reduction in the bone mass is faster in females and structural strength is different for different sexes. Next, initial threshold values, $f_{th}$, are calculated as a function of the input subjective and objective parameters at step 402C. Counter values are then initialized at step 402D.

The next step in the processing is the step of reading the dynamic input signals $f_{ij}$ from the sensory electrodes 201 at step 404. Counter i increases at step 406 as more input information is read, and the current force input data is stored in the j position of the memory buffer 204. At step 408, the input signals are loaded in memory buffer 204 such that the memory buffer pointer j is kept within the range $1 \leq j \leq M$. As shown at step 408A, if the counter I is less than the limit M, the memory pointer J is incremented at step 408C; otherwise, the modulo value for J is calculated at step 408B. The current force input, $F_i$, is then stored in the j position of the memory buffer 204 (F(j)) at step 410.

Once the dynamic input signals are loaded into the memory buffer 2046, the upper and lower threshold limits are calculated at step 412. In particular, if the current force value F(j) is determined at step 412A to be greater than the upper threshold value, a first stimulation signal is outputted at step 412B to encourage the patient to lessen the WB load on the limb, while if the current force value F(j) is determined at step 412C to be lower than the lower threshold value, a second stimulation signal is outputted at step 412D to encourage the patient to increase the WB load on the limb.

Figure 4A:
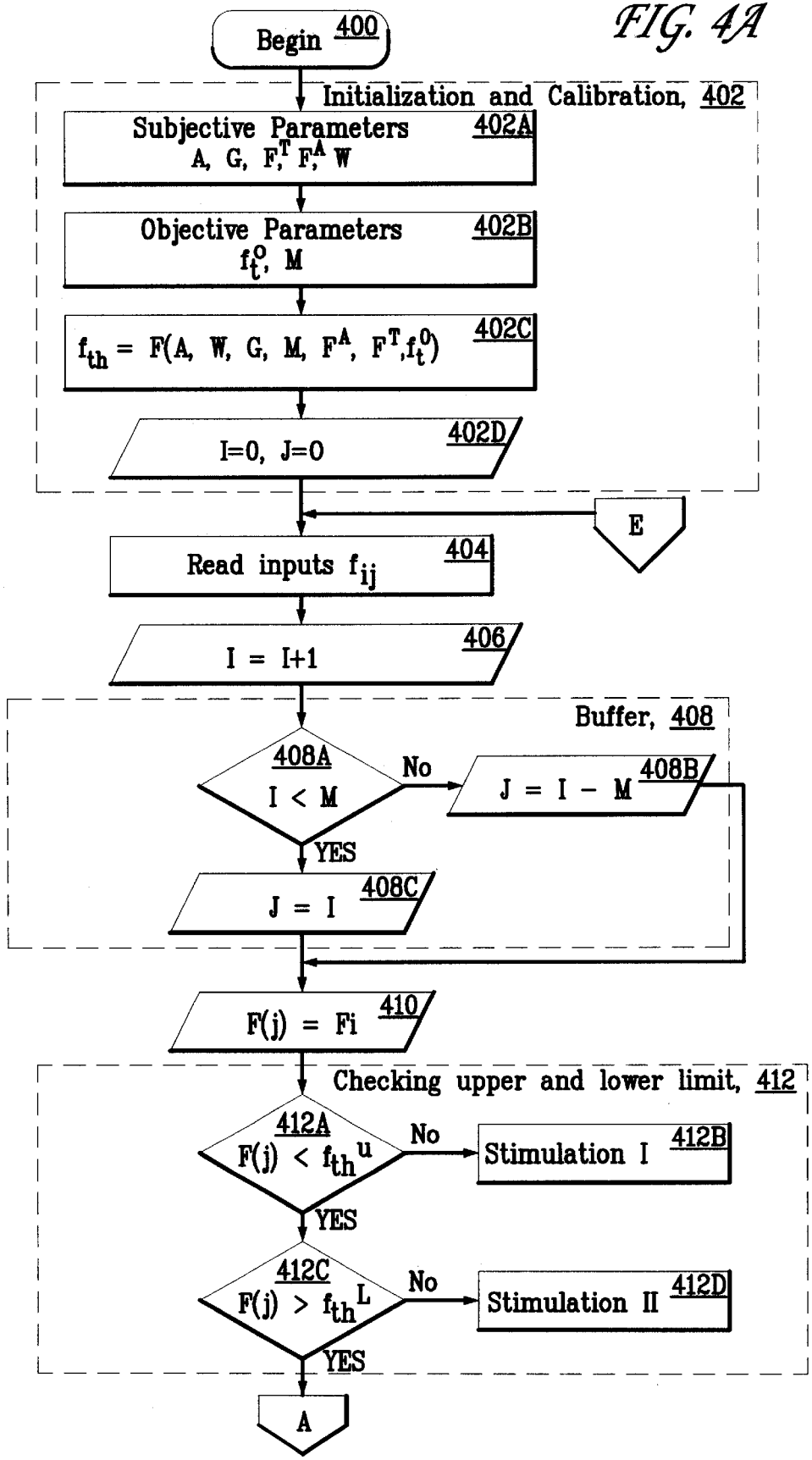
FIGS. 4(A)–4(C) illustrate the software algorithm implemented in the CPU of FIG. 3 for determining when to provide a stimulation signal to the patient's extremity in accordance with the invention.
Figure 4B:
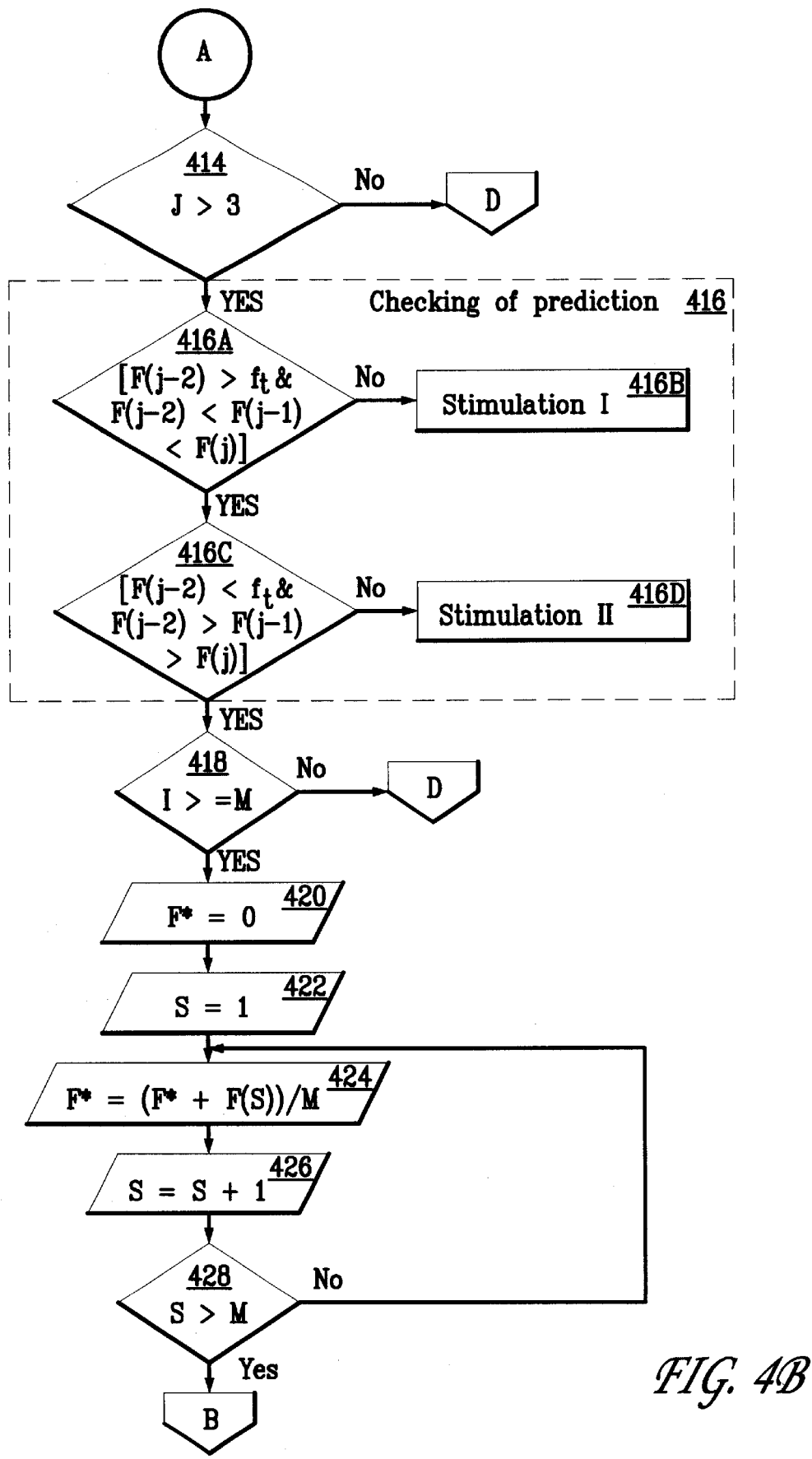

Another condition for stimulation is determined at steps 414 and 416 (FIG. 4(B)). In particular, it is determined at step 414 if at least three dynamic input signal values have been stored. If so, an artificial intelligence subroutine is invoked at step 416 to perform predictive functions. For example, it is determined if three consequentially increasing force values above the target have been received (step 416A), and if the force values are increasing, a first stimulation signal is outputted at step 416B to encourage the patient to lessen the WB load on the limb. It is also determined if three consequently decreasing force values below the target have been received (step 416C), and if the force values are decreasing, a second stimulation signal is outputted at step 416D to encourage the patient to increase the WB load on the limb.

Next, if it is determined at step 418 that the counter value I is greater than or equal to M, another check is performed. Namely, calculations of a standard deviation on M patient steps proceeds at step 420 by initializing the value of F* to zero, setting the standard deviation counter value S equal to 1 at step 422, and then calculating at step 424 the value of F* updated to reflect the changes brought by receiving the first force value F(S), F*=(F*+F(S))/M. The standard deviation counter value S is then incremented at step 426, and it is determined at step 428 whether to repeat the loop to calculate F*. Once the determination is "yes" at step 428, steps 422–428 are then repeated at steps 430–436 for calculation of the second order term F**=F*−F(S))². The standard deviation value for a σ=SQRT(F/M−1) is then determined from these values at step 438. It is then determined at step 440 if the current force value F(j) is within range of ±3σ from the target value. In particular, if the current force value F(j) is determined at step 440A is not within +3σ from the target $f_t-3\sigma \leq f_{ij} \leq f_t+3\sigma$, a first stimulation signal is outputted at step 440B to encourage the patient to lessen the WB load on the limb, while if the current force value F(j) is determined at step 440C to not be within −3σ from the target, a second stimulation signal is outputted at step 440D to encourage the patient to increase the WB load on the limb. At step 442, the target value f(T) is assigned to the current measured center point, and it is determined at step 444 if the power switch to the device has been turned off. If so, processing terminates at step 446; otherwise, the entire loop is repeated again, starting with reading the input sensor signals at step 404**.

Figure 4C:
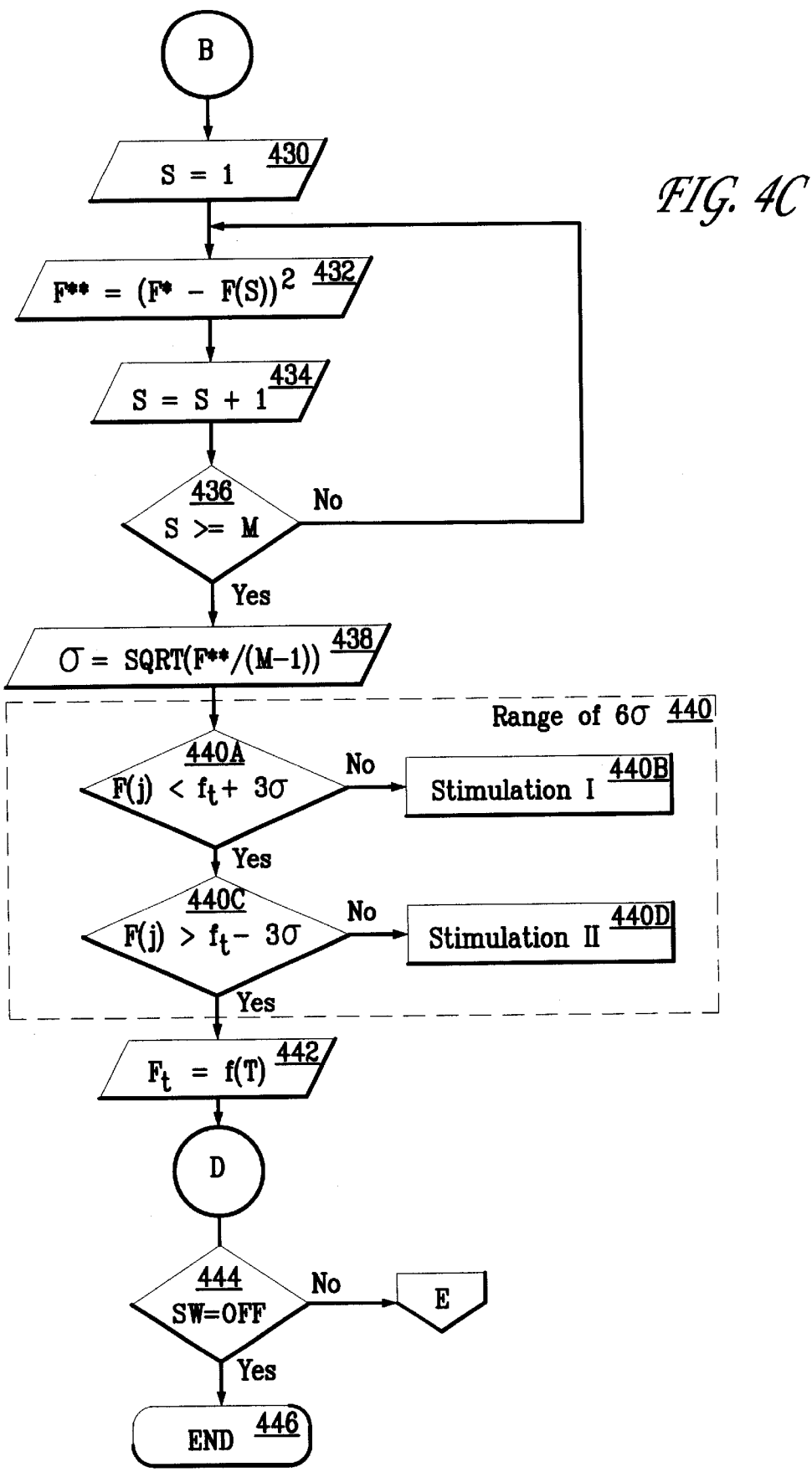

Thus, the algorithm of FIG. 4(A) through FIG. 4(C) causes a stimulation signal to be output when one or more of the following occurs:

an upper threshold violation;

a lower threshold violation;

three consequently increasing control values above the target;

three consequently decreasing control values below the target; and a 6σ range violation.

The biomechanics of bones must be taken into account by the physician when setting the target PWB values in accordance with the invention. For example, it is well known that bone formation is influenced by mechanical stress. As noted by Pauwels, at optimal stress value $\sigma_s$, the constant remodeling of bone tissue is balanced, that is, in a unit of time as much bone tissue is removed by resorption as is built up by apposition. Within the tolerance limit $\sigma_u$ and $\sigma_o$, the apposition will be predominant when the actual stress $\sigma_i$ is greater than $\sigma_s$, while resorption predominates when $\sigma_i$ is below $\sigma_s$. Stresses higher than $\sigma_o$ destroy the bone by pathological resorption, while at stresses below the tolerance limit $\sigma_u$ the resorption ceases and bone is not removed. In addition, an applied force causes stresses and strains in bone. Generally, strains are the stimuli for the remodeling process, and in the balanced steady state (optimal strain), the activity of osteoblast and osteoclast are equal. Lowering of stresses follows strain greater than the optimum to cause bone hypertrophy by a relative predominance of the osteoblast activity and the increase of the load-bearing cross-section. This may lead to strains below the optimum, the predominance of osteoblast that causes atrophy, and the increase in bone stress.

With these biomechanics in mind, those skilled in the art will readily appreciate that different bone parameters may be used by the physician or therapist to characterize each patient's bones structure. Such bones parameters include:

1. Material of construction, including parameters such as Modulus of Elasticity (the slope of the stress-strain curve in the elastic region, or axial rigidity (EA)), strength (the maximal stress at the moment of breakdown of the material), bone density (bone material integrity), the kind of elements (long or short bone), and the specific skeletal element (femur, tibia, etc.);
2. Loading parameters, including load magnitude, loading speed (as long as the load rate is higher the bone is more susceptible to injury), and type (tensile, bending, etc.);
3. Fracture parameters (Fx) including Fx type (simple, complicated, etc.), Fx location (proximal, middle, distal, intrarticular), Fx geometry (shape, dimension), and load type including tensile load (transverse Fx), axial load (oblique Fx), and rotational load (spiral Fx);
4. Fixation or implant parameters including type (plate, intramedular nail, interlocking, external fix, prostheses, etc.), material strength (high or low), and structure including size (dimension), shape, nature and degree of support;
5. Bone/fixation load ratio;
6. Time dependence;
7. Mass of the limb distal to the lesion; and
8. Muscular force around the Fx.

Biochemical parameters are also significant, including metabolic factors such as amount of calcium, phosphorous, vitamins A, C and D and the secretion of the pituitary, thyroid and parathyroid adrenal and gonads.

The above factors, and others, are preferably taken into account by the physician or therapist in setting the target PWB values. Once set, the feedforward processing technique of the invention assures that the target load is applied to the limb by applying the appropriate mechanical or electrical stimulation. Neural networks or other suitable artificial intelligence circuitry may be used to measure and process the dynamic data for a number of steps, to conduct a real-time statistical study, and to generate a signal that guides the next step of the patient through sensory electrical and/or mechanical stimulation (ES) of the patient's body or tissue via mechanical vibration or stimulating electrodes 209. By way of example, such stimulation may be applied to the patient's body in such a way as to alter the patient's weight bearing without requiring the patient to concentrate on graphic displays or to listen for alarms.

Personal Rehabilitation Program

Those skilled in the art will appreciate that the present invention may be used by physiotherapists to develop personal rehabilitation programs for patients. In particular, the physiotherapists may fix personal parameters (age, weight, sex, fracture type, date of injury, etc.), and on the basis of these parameters, the CPU of the system of the invention, or the physiotherapist, may decide which rehabilitation program is the most suitable. The system of the invention then measures the pressure applied on the limb, collects data over time, and decides how the patient should pace. The stimulation signal stimulates the patient to load the optimal weight. The system of the invention also conducts a real time statistical study after a series of steps and corrects the patient by a feedforward stimulation, which reduces the deviation from the patient's program. The feedback may also consist of signals of different frequency that plurally or visually indicate to increase or decrease the load. Those skilled in the art will appreciate that the present invention allows a personal rehabilitation program based on individual characteristics (age, weight, sex, fracture type, etc.) to be modified by self-learning in an objective manner according to accumulated weight bearing time during physical activity in daily life.

In accordance with the invention, improved bone healing is made possible due to adequate but not excessive intermittent loading of a fracture. Improved tissue healing of soft tissue, ligament, meniscus, and amputation wounds is also possible because patients can respond to sensory signals and limit the trauma produced by applying weight to the injured tissue. Also, by increasing accuracy of monitoring and feedback, the occurrence of adverse effects of overloading or underloading, such as the failure of an implant or delayed union or non-union of a fracture, may be substantially reduced.

The present invention also provides the advantage that it allows the patient's rehabilitation to be objectively monitored post-injury, giving the physician or therapist an intelligent tool allowing him or her to follow specific clinical protocols for rehabilitation. Also, by providing a portable, personal, and easy to use system, the present invention allows the user to continue his or her rehabilitation program at home without the need for continuous professional supervision. Also, the active sensory feedback of the invention allows the patient to learn and to perform the desired weight bearing automatically, faster, and with no need to concentrate on graphic or audible feedback as in conventional devices. The present invention also provides for improved clinical control and documentation of compliance with weight-bearing prescriptions. Therapists also may more accurately control and document compliance.

It is to be understood that the apparatus and method of operation taught herein are illustrative of the invention. Those skilled in the art will appreciate that the circuitry of FIGS. 2 and 3 may be included in a small monitoring device that may be placed on or near the patient's injured lower extremity. For example, the monitoring device may be worn on the patient's foot or leg, on the patient's belt, or may be placed nearby for communication with the sensors via wireless communications. These and other modifications may readily be devised by those skilled in the art without departing from the spirit or scope of the invention. All such modifications are intended to be included within the scope of the appended claims.

We claim:

1. An adaptive weight bearing monitoring system for use in rehabilitating injuries to a lower extremity of a patient, comprising:

at least one sensor disposed so as to detect weight forces applied to the lower extremity of the patient and to generate dynamic weight input signals;

a processor responsive to objective parameters unique to the patient or the injury to the lower extremity of the patient to set an input target weight range for weight forces which may be applied to the lower extremity by the patient during the patient's rehabilitation of the lower extremity for optimized rehabilitation of the lower extremity, said processor comparing said dynamic weight input signals to said input target weight range and generating a first output signal when said dynamic weight input signals indicate that a weight force has been applied to the lower extremity which exceeds said input target weight range and generating a second output signal when said dynamic weight input signals indicate that a weight force has been applied to the lower extremity which is less than said input target weight range; and a stimulator responsive to said first and second output signals so as to generate and apply respective first and second stimulation signals to the lower extremity so as to cause the patient to adjust the amount of weight force to be applied to the extremity during the patient's next stride to bring said weight force into said target weight range.

2. A system as in claim 1, wherein said at least one sensor comprises at least one force sensor incorporated into a flexible insole worn inside a shoe.

3. A system as in claim 2, wherein said at least one sensor comprises at least one pressure sensor placed adjacent the lower extremity of the patient.

4. A system as in claim 1, wherein said stimulator comprises an electrical stimulation unit which generates said first and second stimulation signals from said first and second output signals, respectively, and a plurality of stimulation electrodes placed adjacent the lower extremity of the patient so as to apply the first and second stimulation signals to the lower extremity of the patient.

5. A system as in claim 1, wherein said stimulator comprises a mechanical vibrating element which generates said first and second stimulation signals from said first and second output signals, respectively, and applies said first and second stimulation signals to the lower extremity of the patient.

6. A system as in claim 1, further comprising a memory buffer which stores weight force data applied to the lower extremity during at least one of a predetermined period of time and a predetermined number of steps.

7. A system as in claim 6, wherein said processor analyzes weight force data from said memory buffer which has been previously applied to the lower extremity, calculates an optimum weight load for the lower extremity during the patient's next stride, and adjusts said input target weight range to reflect said optimum weight load.

8. A system as in claim 7, wherein said processor implements an artificial intelligence algorithm that is responsive to at least said stored weight force data to calculate said optimum weight load for the lower extremity during the patient's next stride.

9. A system as in claim 6, wherein said processor further determines whether said weight force data applied to the lower extremity during a predetermined number of successive steps exceeds said input target weight range and is increasing and, if so, outputs a third output signal to said stimulator from which said stimulator generates a third stimulation signal for application to the lower extremity, and determines whether said weight force data applied to the lower extremity during a predetermined number of successive steps is below said input target weight range and is decreasing and, if so, outputs a fourth output signal to said stimulator from which said stimulator generates a fourth stimulation signal for application to the lower extremity.

10. A system as in claim 1, wherein said processor further determines whether said weight force data for a current step is $3\sigma$ above a target weight in said input target weight range, and, if so, generates a third output signal from which said stimulator generates a third stimulation signal for application to the lower extremity, and further determines whether said weight force data for a current step is $-3\sigma$ below said target weight in said input target weight range, and, if so, generates a fourth output signal from which said stimulator generates a fourth stimulation signal for application to said lower extremity.

11. A system as in claim 1, further comprising a power supply which provides sufficient power to said system to allow portability of said system.

12. A system as in claim 1, wherein said objective parameters unique to the patient include the patient's age, gender, weight, and time since injury.

13. A system as in claim 1, wherein said objective parameters include the type of injury to the lower extremity and biomechanical properties of fixation of a fracture injury to the lower extremity, including at least one of material of construction, loading parameters, implant parameters, and muscular force around the injury.

14. A method of monitoring rehabilitation of an injury to a lower extremity of a patient, comprising the steps of:

selecting a type of rehabilitation suitable to the patient on the basis of objective parameters unique to the patient, such parameters including at least one of age, weight, gender, injury type, and date of injury;

setting in accordance with said objective parameters an input target weight range for weight forces which may be applied to the lower extremity by the patient during the patient's rehabilitation of the lower extremity for rehabilitation of the lower extremity;

measuring weight forces applied to the lower extremity of the patient and generating dynamic weight input signals;

storing said dynamic weight input signals over a predetermined period of time;

comparing said dynamic weight input signals to said input target weight range and generating a first output signal when said dynamic weight input signals indicate that a weight force has been applied to the lower extremity which exceeds said input target weight range and generating a second output signal when said dynamic weight input signals indicate that a weight force has been applied to the lower extremity which is less than said input target weight range; and stimulating the patient to adjust the amount of weight force to be applied to the extremity in response to said first and second output signals so as to bring the weight force applied to said lower extremity into said target weight range during the patient's next stride.

15. A method as in claim 14, comprising the additional steps of conducting a real-time statistical analysis of dynamic weight input signals stored during said storing step and generating a feedforward electrical stimulation signal based on said real-time statistical analysis.

\* \* \* \* \*

UNITED STATES PATENT AND TRADEMARK OFFICE
CERTIFICATE OF CORRECTION

PATENT NO.     : 6,273,863 B1
DATED          : August 14, 2001
INVENTOR(S)    : Avni et al.

It is certified that error appears in the above-identified patent and that said Letters Patent is hereby corrected as shown below:

<u>Column 8,</u>
Line 66, please delete "plurally" and insert -- aurally --;

Signed and Sealed this

Twenty-sixth Day of March, 2002

*Attest:*

*Attesting Officer*

JAMES E. ROGAN
*Director of the United States Patent and Trademark Office*